United States Patent [19]

Kriesel et al.

[11] 4,340,582

[45] Jul. 20, 1982

[54] ERYTHROMYCIN BASE TABLETS

[75] Inventors: Douglas C. Kriesel, Lake Bluff; Shashi P. Mehta, Libertyville, both of Ill.

[73] Assignee: Abbott Laboratories, North Chicago, Ill.

[21] Appl. No.: 225,214

[22] Filed: Jan. 15, 1981

[51] Int. Cl.$^3$ .................. A61K 9/36; A61K 31/71
[52] U.S. Cl. ...................................... 424/35; 424/181
[58] Field of Search ................................ 424/35, 181

[56] References Cited

U.S. PATENT DOCUMENTS

| | | | |
|---|---|---|---|
| 2,798,024 | 7/1957 | Zapapas et al. | 424/21 |
| 2,864,817 | 12/1958 | Croley | 260/210 |
| 3,242,049 | 3/1966 | O'Brien et al. | 424/19 |
| 3,639,565 | 2/1972 | Prillig | 424/35 |
| 3,784,683 | 1/1974 | Prillig et al. | 424/35 |
| 3,789,117 | 1/1974 | Tsujino | 424/35 |
| 3,865,935 | 2/1975 | Amann | 424/181 |
| 3,960,757 | 6/1976 | Morishita et al. | 424/35 |
| 3,962,419 | 6/1976 | Mayama et al. | 424/35 |
| 3,981,984 | 9/1976 | Signorino | 424/35 |
| 4,001,390 | 1/1977 | Ohno et al. | 424/35 |
| 4,013,820 | 3/1977 | Farhadish et al. | 424/181 |
| 4,017,647 | 4/1977 | Ohno et al. | 424/35 |
| 4,101,651 | 7/1978 | Kobayashi et al. | 424/35 |
| 4,127,647 | 11/1978 | Sato et al. | 424/181 |
| 4,226,981 | 10/1980 | Onda et al. | 424/35 |
| 4,287,221 | 9/1981 | Tonedachi et al. | 424/35 |
| 4,289,751 | 9/1981 | Windheuser | 424/35 |

FOREIGN PATENT DOCUMENTS

| | | | |
|---|---|---|---|
| 8780 | 3/1980 | European Pat. Off. | 424/35 |
| 13566 | 7/1980 | European Pat. Off. | 424/35 |
| 2415490 | 10/1974 | Fed. Rep. of Germany | 424/35 |
| 44-295 | 1/1969 | Japan | 424/35 |
| 44-26319 | 5/1969 | Japan | 424/35 |
| 45-38715 | 12/1970 | Japan | 424/35 |
| 46-29743 | 8/1971 | Japan | 424/35 |
| 49-133515 | 12/1974 | Japan | 424/35 |
| 54-126722 | 10/1979 | Japan | 424/35 |
| 55-83712 | 6/1980 | Japan | 424/81 |

OTHER PUBLICATIONS

Watanabe et al., Nippon Yakugakkai Yakugaku Zasshi, 97(7):791-800, (1977).
Pelizza et al., Il Farmaeo 31(4): 254-263, (1976).
Eckert Pharmazeutische Industrie, 38(9): 836-841, (1976).
Mannisto et al., Arzneimittel-Forschung, 25(11): 1828-1831, (1975).
Robertson et al., J. Pharm. Sci., 61(10):1633-1635, Oct. 1972.
Koroleva et al., Antibiotiki, 14(12):1084-1088, (1969).
Goodwin, Medical Journal of Australia, 1:1280, (1967).
Shtol'ts et al., Antibiotiki, 11(4):291-4, (1966).
Gruber et al., J. Am. Pharm. Assn., 47:867-869, (1958).
Rose Anal. Chem., 26:938-939, (1954).
Bauer et al., Pharmazeutische Industrie, 41(12):1203-1207, (1979).
Dette Infection, (Munich), 7(3):129-145, (1979).
Watanabe et al., Nippon Yakugakkai Yakugaku Zasshi, 98(8):1092-1100, (1978).
Allen et al., J. Pharm. Sci., 67(8):1087-1093, Aug. 1978.
Springolo Bollettino Chimico-Farmaceutico, 117(2):113-121, (1978).
Spitall Pharmazeutische Industrie, 39(5):502-505, (1977).
Chun et al., Infection, 5(Suppl. 1):14-22, (1977).
McDonald et al., J. Clinical Pharmacology, 17(10 pt. 1):601-606, (1977).
Osterwald et al., ACTA Pharmaceutica Technologica, 27(1):47-60, (1981).
Osterwald et al., ACTA Pharmaceutica Technologica, 26(3):201-209, (1980).
DiSanto et al., J. Clin. Pharmacol., 20(7):437-443; (1980).
Piros Gyogyszereszet, 24(12):460-466, (1980).
Yakatan et al., J. Pharmacokinetics Biopharmaceutics, 7(4):355-368, (1979).
Watanabe et al., Nippon Yakugakkai Yakugaku Zasshi, 99(3):308-314, (1979).
Tomasini et al., Farmatsiya, (Sofia), 29(2):16-22, (1979).
Bechtol et al., Current Therapeutic Research, 25(5):618-625, (1979).

*Primary Examiner*—Shep K. Rose
*Attorney, Agent, or Firm*—Robert L. Niblack; Paul D. Burgauer

[57] ABSTRACT

An enteric coated erythromycin tablet is provided that produces essentially the same blood levels in fasting and nonfasting subjects. The tablet contains erythromycin base dihydrate and a highly water-soluble nontoxic salt in the core and the coating polymer is a hydroxypropyl methylcellulose phthalate.

9 Claims, No Drawings

ERYTHROMYCIN BASE TABLETS

DETAILED DESCRIPTION OF THE INVENTION

Erythromycin has been a leading antibiotic for many years and recently, more of the manufacturers for several reasons are providing erythromycin in the form of the simple base, in contrast of previous esters and salts. Unfortunately, erythromycin is sensitive to the juices of the stomach and if exposed to the high acidity there, only very little of the dosage administered to a warm-blooded animal passes into the blood stream. A common solution to this problem is to apply an enteric coating to the tablet cores containing the antibiotic.

Some of the currently marketed erythromycin base tablets have been provided with enteric coatings or similar systems which prevent premature degradation in the digestive system. Most of these tablets must be ingested on a fasting stomach in order to provide adequate blood levels. Also, some of the currently available erythromycin tablets are provided with an enteric coating which have prolonged dissolution rates after long term storage. These and other factors cause some of the marketed erythromycin tablets to show erratic absorption.

It has now been found that the above difficulties can be overcome by providing an enteric coated erythromycin base tablet consisting essentially of a tablet core and a tablet coating, said core consisting essentially of 250 parts of erythromycin base in the form of its dihydrate, 35 to 100 parts of a water soluble nontoxic ingestible salt, and 40 to 175 parts of the usual tableting excipients including diluents, binders, disentegrants and lubricants, said core being coated from a hydro-alcoholic solvent containing, per table core, 16 to 25 parts of hydroxypropyl methylcellulose phthalate (hereinafter referred to as HPMCP) and 1 to 10 parts of customary coating excipients including dyes, pigments and plasticizers. All references to "parts" herein and hereinafter is based on weight parts.

A preferred range of components, based on a 250 mg. erythromycin tablet, comprises 40-65 mg. of lubricants and/or glidants, 65-105 mg. of the other mentioned tableting excipients and the mentioned range of HPMCP Type 55 polymer.

A preferred hydro-alcoholic coating solvent is an ethanol/water mixture in a volume ratio of about 4:1. Such a coating vehicle has the advantage that it readily evaporates and does not produce the environmental objections of ketonic or halogenated solvents often used in such an operation. Mixtures of alcohol and water of different proportions can be used with equivalent results, e.g., those solutions containing 40-95% alcohol. However, when the alcohol proportion is below about 60%, the HPMCP does not dissolve, it is easily dispersible though, and forms a continuous film as if it were applied from a solution. Among the pigments, Titanium dioxide is the most commonly used pigment (and opaquing agent). It is usually used along with pharmaceutically acceptable colorants.

The most important ingredient of the tablet coating mixture is the above-mentioned film-forming polymer. In order to give the most satisfactory and uniform absorption patterns, a HPMCP polymer is used which contains between 32 and 33 percent of phthalyl groups, 18.5 to 19 percent of methoxy groups and 6 to 7 percent of hydroxypropoxy groups. HPMCP of this nature dissolves readily at a pH of 5.5; it is commercially available as Hydroxypropyl Methyl Cellulose Phthalate Type HP 55. This kind of HPMCP produces highly satisfactory, uniform and coherent films over the tablets, protecting them through the residence in the stomach of a warm-blooded animal when said coating is applied in an amount of at least 16 mg. per tablet. No advantage is gained by using more than 25 mg. of the above HPMCP per tablet. This is in sharp contrast to other HPMCP's which, even when applied in amounts as high as 40 mg. per tablet do not provide proper enteric properties. The defined HPMCP also differs from previously used enteric coating polymers in thermal stability and in providing a true, enteric, coherent film. In comparison, cellulose acetate phthalate has been used successfully for enteric coating but lacks long-term storage stability; hydroxypropyl methylcellulose, another frequently used tablet coating polymer, is perfectly stable but does not form an enteric coating.

The above-mentioned tablet core must contain the erythromycin base in the form of its dihydrate; it has been learned that only the dihydrate produces a desirable, uniform blood levels. The other major requirement concerns the water soluble, ingestible, nontoxic salt; excellent results are obtained by using potassium chloride, sodium citrate or similar highly water soluble materials that are easily tolerated by the digestive tract of warm-blooded animals. Other ingredients usually used in the preparation of tablet cores comprise, per 250 part of active erythromycin base, about 10 to 50 parts of a pharmaceutically acceptable diluent, e.g., starch or microcrystallinecellulose; 2.5 to 12 parts of a pharmaceutically acceptable binder such as starch, polyvinylpyrrolidone, sodium carboxymethylcellulose and the like; and glidants or lubricants, for instance, talcum powder, a pharmaceutically acceptable silicone, stearic acid or a nontoxic metal stearate. These materials are compressed into tablets in the usual fashion by granulating the drug, starch, water soluble salt and part of the diluent and subsequently compressing the granules together with the glidant/lubricant and other excipients into cores of desired shape and hardness. As disintegrants, one often uses soy polysaccharides, an ion exchange resin, cross-linked polyvinyl pyrrolidone, sodium starch glycolate or the like. The coating solution is subsequently applied in standard fashion, using the classic pan coating or air suspension coating techniques.

If desired, the coated tablet can be provided with a clear coating, which contains essentially the same ingredients as the above-defined coating except for the absence of pigments and dyes. A simple clear coating mixture contains, per 250 parts of erythromycin base in the core, 2.7 to 4.1 part of HPMCP, 0.25 to 0.4 parts of a plasticizer and 0.25 to 0.4 parts of a flavoring component or components in a hydro-alcoholic system.

The preferred nontoxic, water soluble ingestable component of the tablet core is sodium citrate, although many other highly water soluble materials can be used, including potassium chloride which is often substituted for sodium citrate.

In order to illustrate the manufacture of a tablet of the above definition, reference is made to the following example, which, however, is not meant to limit the invention in any respect.

EXAMPLE

Tablet A. A solution of 3 grams of polyvinyl pyrrolidone in 60 ml. of water was used to granulate a uniform blend of 277.8 grams of erythromycin base dihydrate, 25 grams of micro-crystalline cellulose, and 41 grams of sodium citrate. The lumpy mass obtained was broken up, spread on paper lined trays, dried and screened through a 16-mesh screen.

Separately, 40.2 grams of soy polysaccharides, 5 grams of talcum powder and 6 grams of magnesium stearate were blended uniformly and screened through a 16-mesh screen. This mixture was then added to the above dried granules, mixed and compressed into ovaloid shaped tablets weighing 398 mg. per tablet.

A portion of a solution made from 191 ml. of ethanol and 48 ml. of water was used to mill 0.12 grams of Red DC Lake #30 and 1.8 grams of titanium dioxide to a uniform slurry. Separately, 19.1 grams of HPMCP and 1.5 grams of distilled acetylated monoglyceride were dissolved in a portion of the ethanol/water mixture and this solution was combined with the above red pigment mixture. The volume was adjusted to 239 ml. with the remaining hydro-alcoholic mixture. This coating solution was then applied to the above tablets in the usual fashion in a pan coater at 60° C. temperature to provide the desired enteric coated tablets.

A clear coating was subsequently applied to the above coated tablets in the above fashion from a solution containing 3.2 grams of HPMCP, 0.3 grams of distilled acetylated monoglyceride, 0.3 grams of vanillin in 64 ml. of ethanol and 16 ml. of water.

Tablet B. A tablet core was prepared in the same fashion as the one described above, except that for the same amount of drug, 100 grams of lactose monohydrate, 34 grams of corn starch, 45 grams of Amberlite IRP 88 and 6 grams of magnesium stearate were used. These cores were compressed in the same fashion to the same hardness as under A above, and then coated with the identical color enteric coating solution and clear enteric coating solution as described above.

Tablet C. Another tablet was made using lactose as the water soluble component, but in place of the HPMCP, a cellulose acetate phthalate derivative was used which does not carry hydroxypropyl and methyl groups.

The three tablets were tested in identical fashion by 21 adult subjects receiving 5 dosages of 1 tablet each every six hours on a fasting stomach, and a sixth tablet, 30 hours after the first tablet, of the identical composition but under nonfasting conditions. In all instances, blood samples were taken regularly to determine the peak concentration of erythromycin in blood serum, and to determine the area-under-the-curve (AUC) for each.

The medium time for achieving the maximum erythromycin blood level for tablets A and B were 27 hours; for tablet C is was 28 hours. More significantly, the time range in which the peak occurred for tablet A was 26 to 28 hours for the 21 subjects; for tablet B, the range was 26 to 29 hours and for tablet C, the spread was between 24 and 30 hours.

The maximum concentration was measured in mcg/ml in blood serum and revealed, for tablet A, an average of 1.899 with a deviation of 0.895; for tablets B and C, the values were 1.958 (0.689) and 1.681 (1.143), respectively. The AUC over the first 30 hours for tablet A was 5.88; tablets B and C showed values of 5.74 and 5.41 respectively.

It is established with the above comparison that under fasting conditions, tablets A and B are somewhat similar, with both of them showing more uniform (less deviation) results than tablet C.

The sixth dose was administered on a nonfasting stomach. Table I shows the blood levels obtained at the hours indicated, said hours being counted from the start of the administration to each subject. In each instance, the standard deviation is shown in parenthesis: All values are given in mcg/ml blood serum; $T_{max}$ and $C_{max}$ indicate mean values at the time at which individual maximum concentrations occurred and the individual maxium blood levels.

TABLE I

| Time hrs. | A mcg/ml | B mcg/ml | C mcg/ml |
|---|---|---|---|
| 30 | 0.600 (0.304) | 0.581 (0.260) | 0.667 (0.335) |
| 31 | 0.441 (0.263) | 0.408 (0.198) | 0.510 (0.303) |
| 32 | 0.397 (0.414) | 0.449 (0.614) | 0.394 (0.222) |
| 33 | 0.685 (1.183) | 0.496 (0.546) | 0.396 (0.432) |
| 34 | 0.503 (0.641) | 0.356 (0.312) | 0.366 (0.443) |
| 35 | 0.413 (0.505) | 0.343 (0.347) | 0.300 (0.266) |
| 36 | 0.645 (0.739) | 0.379 (0.451) | 0.457 (0.672) |
| 38 | 0.361 (0.246) | 0.260 (0.221) | 0.389 (0.284) |
| $T_{max}$ | 33 (30–38) | 30 (30–38) | 32 (30–36) |
| $C_{max}$ | 1.387 (1.176) | 1.025 (0.614) | 1.008 (0.684) |
| AUC(hrs) | | | |
| 30–38 | 4.07 (3.02) | 3.17 (1.82) | 3.37 (2.12) |
| 30–36 | 3.06 (2.53) | 2.53 (1.66) | 2.53 (1.56) |
| 24–38 | 9.95 (5.09) | 8.91 (2.96) | 8.79 (4.03) |

In a second study, carried out with 23 fasting subjects, a single tablet was administered and the blood levels were determined in the fashion shown above, producing the results indicated in Table II.

TABLE II

| Time hrs. | A mcg/ml | B mcg/ml | C mcg/ml |
|---|---|---|---|
| 1 | 0.022 (0.105) | 0.127 (0.266) | 0 (0.000) |
| 2 | 0.211 (0.263) | 0.310 (0.331) | 0.012 (0.038) |
| 3 | 0.860 (0.547) | 0.655 (0.493) | 0.592 (0.707) |
| 4 | 0.521 (0.281) | 0.372 (0.242) | 0.440 (0.488) |
| 5 | 0.388 (0.304) | 0.241 (0.150) | 0.281 (0.232) |
| 6 | 0.266 (0.140) | 0.151 (0.100) | 0.238 (0.127) |
| 8 | 0.136 (0.061) | 0.076 (0.052) | 0.163 (0.135) |
| 12 | 0.039 (0.031) | 0.015 (0.021) | 0.047 (0.032) |
| $T_{max}$ | 3.0 (3 to 6) | 3.0 (1 to 4) | 4.0 (3 to 8) |
| $C_{max}$ | 0.945 (0.519) | 0.737 (0.483) | 0.814 (0.663) |
| AUC(hrs) | | | |
| 12 | 2.89 (1.11) | 2.19 (1.23) | 2.27 (1.28) |

It will be seen from Table II that the maximum blood level for tablet A is considerably higher than with tablets B and C and that the area under the curve for tablet A is far superior to B and C with the AUC also showing a smaller deviation within the subjects.

In a still further experiment, 21 subjects were given a single tablet under nonfasting conditions with equivalent blood serum measurements being made as before. The results are reproduced in Table III.

TABLE III

| Time hrs. | A mcg/ml | B mcg/ml | C mcg/ml |
|---|---|---|---|
| 1 | 0.415 (0.721) | 0.085 (0.223) | 0 |
| 2 | 0.678 (0.932) | 0.137 (0.205) | 0 |
| 3 | 0.538 (0.465) | 0.180 (0.231) | 0.048 (0.153) |
| 4 | 0.588 (0.544) | 0.097 (0.588) | 0.170 (0.276) |
| 5 | 0.463 (0.333) | 0.075 (0.115) | 0.378 (0.428) |

TABLE III-continued

| Time hrs. | A mcg/ml | B mcg/ml | C mcg/ml |
|---|---|---|---|
| 6 | 0.435 (0.488) | 0.276 (0.492) | 0.588 (0.373) |
| 8 | 0.152 (0.106) | 0.090 (0.155) | 0.329 (0.246) |
| 12 | 0.025 (0.027) | 0.017 (0.032) | 0.065 (0.041) |
| $T_{max}$ | 3 (1 to 6) | 3 (1 to 6) | 6 (3 to 8) |
| $C_{max}$ | 1.535 (0.624) | 0.470 (0.478) | 0.755 (0.363) |
| AUC(hrs) 0-12 | 3.84 (1.23) | 1.29 (1.25) | 2.59 (1.20) |

It is clearly seen from the above table that formulation A is far superior in nonfasting subjects than either of the other formulations; the maximum blood level obtained is more than twice that of formulation C and almost three times that of B, while the area under the curve for A is 50% and 200% better, respectively than formulations B and C.

The above formulation A can be modified within the ingredient ranges shown in the above definition, as will be readily appreciated by those skilled in the art. Various replacements of dyes, pigments, coating ingredients and diluents produce basically the same beneficial results shown for A above, in all instances being far superior to C and often equally superior to B. The main features that must be kept for all possible variations to produce the desirable results achieved before, are the use of erythromycin base in the form of its dihydrate, the use of HPMCP as the film forming polymer in the enteric coating solution and the use of a highly water soluble, orally nontoxic salts as a diluent of said erythromycin base.

We claim:

1. An enteric coated erythromycin base tablet consisting essentially of a tablet core and a tablet coating, said core consisting essentially of 250 parts of erythromycin base in the form of its dihydrate, 35 to 100 parts of a highly water soluble orally nontoxic ingestible salt, and 40 to 165 parts of lubricants, binders, diluents and disintegrants, and said core being coated from a solution consisting essentially of 16 to 25 parts of hydroxypropyl methylcellulose phthalate in an ethanol/water mixture containing pigments, plasticizers, dyes and flavoring agents, said core forming an integral and impervious envelope over said core, and, if desired, a further, outer and clear coating applied from a solution containing said hydroxypropyl methylcellulose phthalate, plasticizer and flavoring components in an ethanol/water mixture.

2. The tablet of claim 1 wherein said ingestible nontoxic salt is sodium citrate.

3. The tablet of claim 1 wherein said orally nontoxic salt is potassium chloride.

4. A tablet according to claim 1 wherein said water soluble nontoxic salt is present in an amount of 40-65 parts and said lubricants, binders, diluents and disintegrants are present in an amount of 65-105 parts.

5. The tablet of claim 4 wherein said water soluble nontoxic salt is sodium citrate.

6. The tablet of claim 4 wherein said water soluble nontoxic salt is potassium chloride.

7. The process of making an erythromycin base tablet core comprising the steps of (a) preparing a tablet core consisting essentially of 100 parts of erythromycin base dihydrate, 8-32 parts of a highly water soluble, orally nontoxic salt, 1-5 parts of a pharmaceutically acceptable binder, 8-32 parts of a pharmaceutically acceptable disintegrant, and 2-9 parts of tableting glidants and lubricants, (b) compressing said component in the usual fashion into the shape of a pharmaceutical tablet, and (c) coating said tablet from a mixture containing 6.4-10 parts of hydroxypropyl methylcellulose phthalate, 0.6-1.0 parts of one or more plasticizers, 0.04-0.06 parts of a water soluble dye or dye mixture, 0.6-0.9 parts titanium dioxide in 80-125 parts of a 75-85% aqueous ethanol, and if desired, (d) applying a clear outer coating to said coated tablet from a coating mixture containing 6.4-10 parts of hydroxypropyl methylcellulose phthalate, 0.6-1.0 of a plasticizer and optional flavoring agents in a 75-80% aqueous ethanol vehicle.

8. The process of claim 7 wherein said non-toxic salt is sodium citrate.

9. The process of claim 7 wherein said non-toxic salt is potassium chloride.

* * * * *

UNITED STATES PATENT AND TRADEMARK OFFICE
CERTIFICATE OF CORRECTION

PATENT NO. : 4,340,582
DATED : July 20, 1982
INVENTOR(S) : Douglas C. Kriesel, et al.

It is certified that error appears in the above—identified patent and that said Letters Patent is hereby corrected as shown below:

Claim 1, line 1, column 6, delete "core" and substitute therefor -- coating --.

Signed and Sealed this

Twenty-first Day of September 1982

[SEAL]

Attest:

Attesting Officer

GERALD J. MOSSINGHOFF

Commissioner of Patents and Trademarks